United States Patent [19]

Sisti et al.

[11] Patent Number: 4,508,685

[45] Date of Patent: Apr. 2, 1985

[54] MODIFIED-FLAME THERMIONIC DETECTOR FOR GAS CHROMATOGRAPHS AND METHOD FOR THE IDENTIFICATION OF COMPONENTS IN SAMPLE UNDER ANALYSIS

[75] Inventors: Giorgio Sisti; Giuseppe Verga, both of Milan, Italy

[73] Assignee: Carlo Erba Strumentazione S.p.A., Milan, Italy

[21] Appl. No.: 382,313

[22] Filed: May 26, 1982

[30] Foreign Application Priority Data

Jun. 9, 1981 [FI] Finland ................. 8122199

[51] Int. Cl.³ .................................. G01N 21/72
[52] U.S. Cl. ...................... 422/54; 324/470; 422/89; 436/154
[58] Field of Search ................... 422/54, 89; 324/464–470; 436/154

[56] References Cited

U.S. PATENT DOCUMENTS

| | | | |
|---|---|---|---|
| 3,661,533 | 5/1972 | David et al. | 422/54 |
| 3,677,709 | 7/1972 | Reidmann et al. | 422/54 |
| 3,852,037 | 12/1974 | Kolb et al. | 422/54 |
| 3,925,023 | 12/1975 | Kaiser | 422/54 |

Primary Examiner—Michael S. Marcus
Attorney, Agent, or Firm—Millen & White

[57] ABSTRACT

The invention relates to a modified-flame thermionic detector for gas chromatographs, of the type including a burner nozzle, an excitation electrode and a collecting electrode. The electrical connections of the nozzle and the excitation electrode can be changed at the operator's will, together with the spatial position of the excitation electrode with respect to the flame and the collector, to find out the presence of certain compounds, leaving all other conditions of analysis performance and detector supply unaltered. This allows obtaining chromatograms of unknown samples under different conditions of the detector configuration, to put into evidence the presence of certain compounds in the sample by comparing peaks of chromatograms obtained under said different operating conditions of the detector.

8 Claims, 8 Drawing Figures

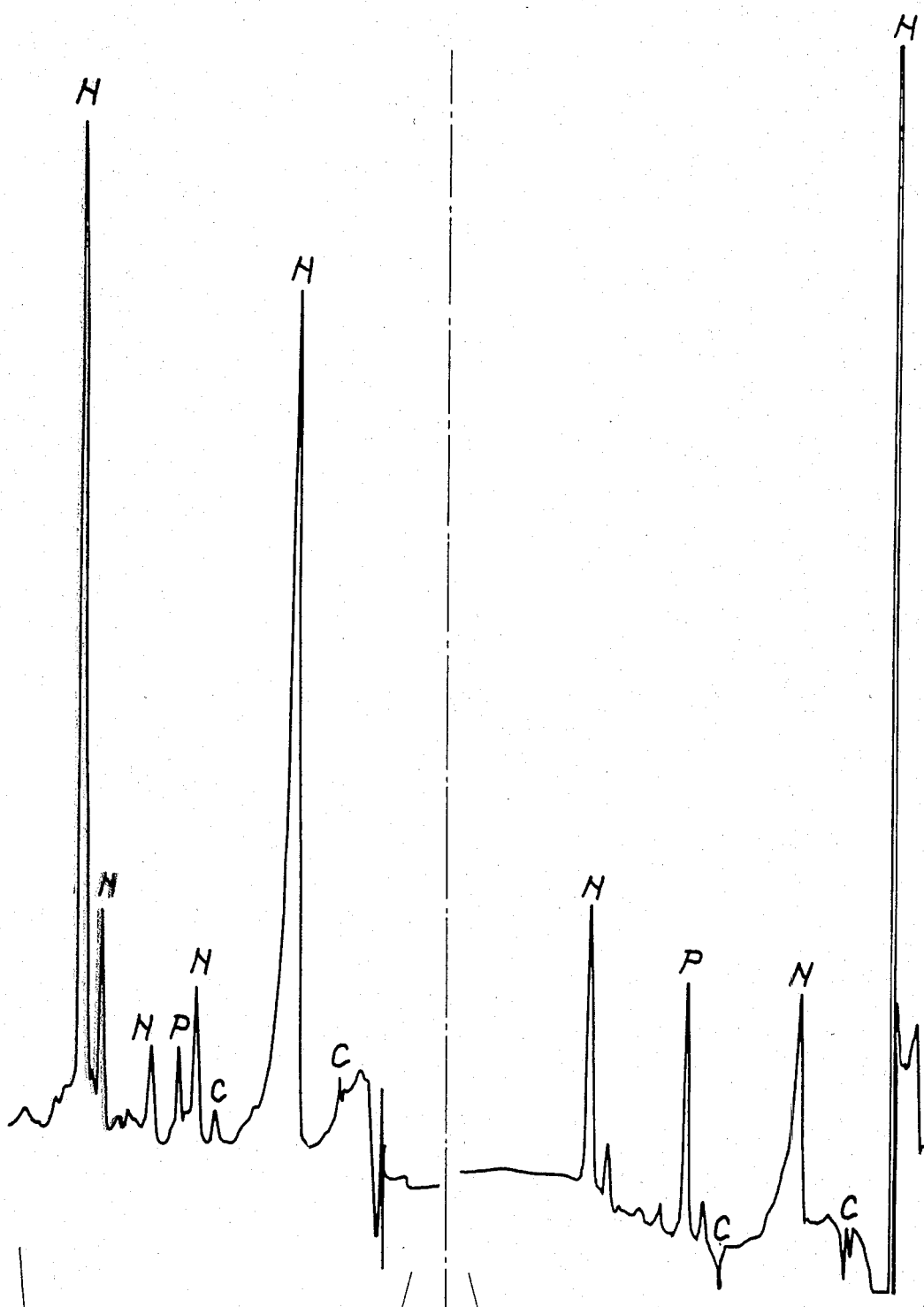

MODIFIED-FLAME THERMIONIC DETECTOR FOR GAS CHROMATOGRAPHS AND METHOD FOR THE IDENTIFICATION OF COMPONENTS IN SAMPLE UNDER ANALYSIS

BACKGROUND OF THE INVENTION

1. Field of the Invention

The present invention relates to a modified-flame thermionic detector for gas chromatographs, of the type including, in a way known in itself, a burner nozzle fed with eluent gas from the chromatograph and with a combustible gas, a collecting electrode coaxial with the flame and connected to a recorder of the current emitted by the same, as well as an excitation electrode comprising an alkali source of thermions, placed on the flame axis, between the latter and the collector.

2. Description of the Prior Art

Modified-flame thermionic detectors of the above mentioned type are already known and used in gas chromatography, for instance as indicated in the U.S. Pat. No. 3,852,037. The detector illustrated in this patent includes an excitation electrode consisting of a glass containing alkali, which is heated to obtain ion emission. In this U.S. patent there is the possibility of modifying the ion-emitting alkali substance, of modifying the nozzle connection to the negative potential of an electric circuit in continuous current or to ground respectively, as well as especially of modifying the combustible gas flow (and also the combustion gas, for instance air) supplied to the nozzle, to determine higher or lower selectivity of the detector with respect to certain substances, in particular to determine the possibility of commutating the detector from its functioning as normal flame ionization detector (FID) to a detector with particular sensibility to halogens and phosphorus. There is also indicated the possibility of using the detector as a detector sensitive to nitrogen compounds, though without use of the flame but with heating by means of electric resistance of the excitation electrode. This detector according to U.S. Pat. No. 3,852,037 allows obtaining chromatograms in which the presence of a certain component is found out, in particular phosphorus and/or nitrogen compounds, but however, this is achieved by considerably modifying the operating conditions of the detector which requires a deep study of the situation from the operator, and in practice at least rough preexisting knowledge of the sample to be analysed on the basis of which the detector must be adjusted.

In case the sample is unknown, it is necessary to perform various subsequent test analyses until one finds the best conditions of electrical connection of the detector parts, of supply of gases to the nozzle and of flame ignition or not, which involves heavy losses of time and the possibility of obtaining wrong results.

Another detector of the known technique, which was used to try to enhance the sensitivity to certain compounds, is illustrated by the U.S. Pat. No. 3,585,003, which describes a detector having a nozzle and a collecting electrode, as well as a couple of so-called "barrier" electrodes, disposed on one side and on the other of the collector. By varying the potential of the barrier electrodes, in this case under constant conditions of gas supply to the flame nozzle, it is possible to obtain a certain variation in sensitivity, particularly to phosphorus-containing compounds. This variation is, however, extremely reduced and of little significance, as it can be noticed in the chromatograms reported in the text of the mentioned U.S. patent.

Finally, another type of detector is known, illustrated in U.S. Pat. No. 3,677,709, which includes a flame nozzle and a ring-shaped collecting electrode, which supports a piece of alkali salt acting as ion-emitting substance. According to this patent, the flame nozzle and the collecting electrode are reciprocally adjustable, so that it is possible, by a suitable reciprocal movement, to change the salt supported by the collecting electrode and to modify the flow in particular of the combustible gas (usually hydrogen), to obtain a certain sensitivity particularly to carbon-containing compounds, which may also give negative peaks on the chromatogram (see FIGS. 6 and 7 of the U.S. Pat. No. 3,677,709).

From the preceding review of the present techniques in the field, it becomes clear that, even if several attempts have been carried out to obtain flame detectors having different sensitivities and variable sensitivity with respect to compounds containing different elements, the results obtained have been rather poor, in that it was generally possible to enhance sensitivity to compounds containing only one particular element, and this with extremely complex, difficult and uncertain regulations.

SUMMARY OF THE INVENTION

Accordingly, an object of the present invention is to provide a new modified-flame thermionic detector for gas chromatographs, of the just described type, which has a configuration such as to allow its adjustment, in a very simple and pratical manner, to respond to the presence of several types of compounds, containing different substances, in particular compounds of phosphorus, nitrogen and carbon, with the possibility however, of operating in conditions corresponding to those of normal flame ionization detectors (FID).

Another object of the present invention is to propose a new thermionic detector of the above mentioned type, which can be adjusted to respond to compounds containing one or more determined chemical elements (P and N) on the basis of simple regulations of mechanical and/or electrical type to be performed on the detector itself and by the operator without a need of knowing a priori the sample to be analyzed. In particular, the invention has the purpose of proposing a new detector which is selective with respect to compounds of nitrogen, phosphorous or carbon and which may be set in a selective position towards one or more of these compounds without need of flow regulations, in particular, without need of adjusting the flowrate of the combustible gas supplied to the nozzle.

Still a further object of the present invention is to propose a new method for the identification of components in an unknown sample by means of gas chromatographic analysis and detection of the eluent thanks to a detector according to the invention itself, which allows determination of the desired components in a very simple and quick manner by comparison of a very reduced number of chromatograms, obtained after analysis performed on the same sample, under different detecting conditions.

According to the invention, these and others objects are achieved with a flame thermionic detector of the type and for the uses hereinabove described, in which essentially the nozzle and the excitation electrode of the same are inserted in an electric circuit in continuous current, comprising a switch to alternatively select at least two different positions of circuital connection and/or electric insulation of the same: and in which the excitation electrode is mounted on a mobile support to position said electrode along the flame axis, between the nozzle and the collector. In other words, according to the invention, it has been surprisingly noticed that it is possible to obtain a selectivity of the detector to compounds of nitrogen, phosphorous, of phosphorous and nitrogen, as well as of carbon, keeping all the other conditions unchanged and simply moving the excitation electrode near to or far from the collecting electrode (or the flame nozzle) and varying the conditions of circuital connection and/or electric insulation of the flame nozzle and of said exciting electrode. In particular, said electric circuit comprises a three-position switch, the first position corresponding to the connection of the nozzle and the excitation electrode to the circuit negative potential, the second position corresponding to the connection of the nozzle to the negative potential and to the electrical insulation of the electrode with respect to the circuit and finally the third position corresponding to the connection of the electrode to the circuit negative potential and to the connection of the nozzle to ground. These three conditions correspond, as it will be better seen later on, to the following three conditions respectively: sensitivity of the detector both to nitrogen-containing compounds and to phosphorus containing compounds, sensitivity of the detector to phosphorous containing compounds and finally sensivity of the detector of nitrogen-containing compounds. Parallel and jointly to what has been said above, a movement of the excitation electrode towards the collecting electrode increases the detector response to carbon compounds, while a removal from it decreases such response as far as to bring the latter to form a negative peak in the chromatogram, which allows immediate identification of these carbon compounds. What is said above always occurs keeping constant the combustible gas flow, preferably hydrogen, as well the flow of the combustion gas which is preferably air, while the sample carrier gas, also supplied to the nozzle, is advantageously constituted by helium.

It is now clear that, suitably varying the detector conditions according to the invention, it is possible, with an extremely reduced number of chromatograms, in the best cases with only two chromatograms, to obtain the identification of components of an unknown sample, by simply comparing the peaks of the chromatograms themselves obtained under said different detector conditions.

BRIEF DESCRIPTION OF THE DRAWINGS

FIGS. 7 and 8 are two chromatograms obtained on the same sample, different from that of the preceding figures, obtained with different adjustments of a detector according to the invention.

DESCRIPTION OF THE PREFERRED EMBODIMENT

Figure 1:
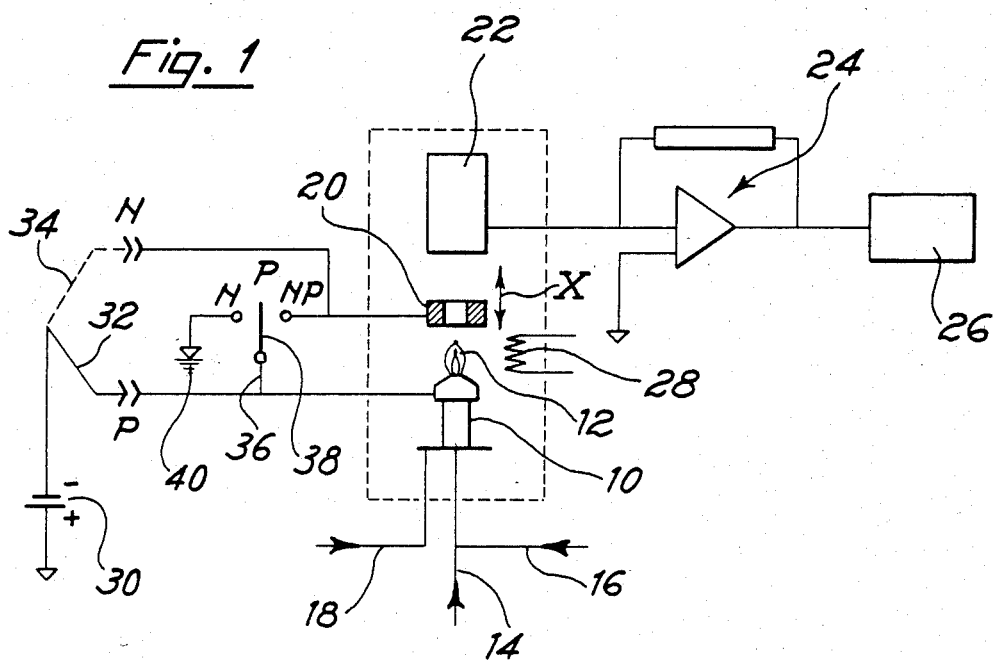
FIG. 1 diagrammatically illustrates the detector according to the invention.

Referring to the drawings and first of all to FIG. 1, it is seen that it schematically illustrates a thermionic detector of the modified-flame type according to the invention. This detector comprises, in a known manner, a nozzle 10 capable of forming a flame 12, which is supplied with the gas from the gas chromatographic column via a conduit 14, to which a second conduit 16 is connected to supply the combustible gas, in particular hydrogen, coming from a suitable source (not illustrated).

The nozzle 10, or directly the flame 12, is also supplied with a combustion gas, in particular constituted by air, as indicated by 18. Coaxially to the nozzle 10 and therefore, to the flame 12, above the latter, an excitation electrode 20 is disposed, comprising a thermionic alkali source, which can be of any suitable type, known in itself. Always coaxially to the nozzle 10, to the flame 12 and to the excitation electrode 20, the detector comprises a second collecting electrode 22 which is connected, via an amplifier 24, to a recorder 26 which records the electrical signal coming from the collector, forming the peak chromatogram, known in itself. Any suitable means, schematically shown by 28, can be used to control flame ignition. Always in a known manner, the collecting electrode is electrically connected in such a way as to result positive both with respect to the excitation electrode 20 and to the nozzle 10.

As shown in FIG. 1, the excitation electrode 20 and nozzle 10 are connected to an electric circuit in continuous current, supplied by a source 30, the negative potential of which can be connected, alternatively or jointly, to a wire 32 which reaches the nozzle 10, or to a wire 34 which is connected to the excitation electrode 20. A shunt 36 on the wire 32 leads to a switch, schematically indicated by 38, which operates jointly with a means (not-shown) capable of circuitally connecting the wire 32 or the wire 34. The switch 38 has three positions, and namely a first position, indicated by N on the drawing, in which the wire 34 of the circuit is connected to the negative potential of the source 30 and therefore to the excitation electrode 20, while the nozzle 10 is connected through the shunt 36, to the ground 40. The second position of the switch is illustrated in FIG. 1 and indicated by P, in which the nozzle 10 is connected to the negative potential of the source 30 through the shunt 32, while the wire 34 is disconnected and therefore, the excitation electrode 20 is electrically insulated with respect to this circuit and to the detector mass. Finally, the switch 38 can be set in the position indicated by NP, in which the electrode 20 and the nozzle 10 are both connected with the negative potential of the source 30, through one or the other of the wires 32 or 34.

Still according to the invention, as schematically illustrated by the double arrow X, the excitation electrode 20 can be moved, by means of a support on which it is mounted, axially from or towards the collecting electrode 22, in order to change, as it will be better seen later on, the response to carbon compounds. In particular, approaching the electrode 20 to the electrode 22 the response to carbon increases, while removing these two electrodes from each other the response decreases until negative peaks are obtained.

Figure 2:
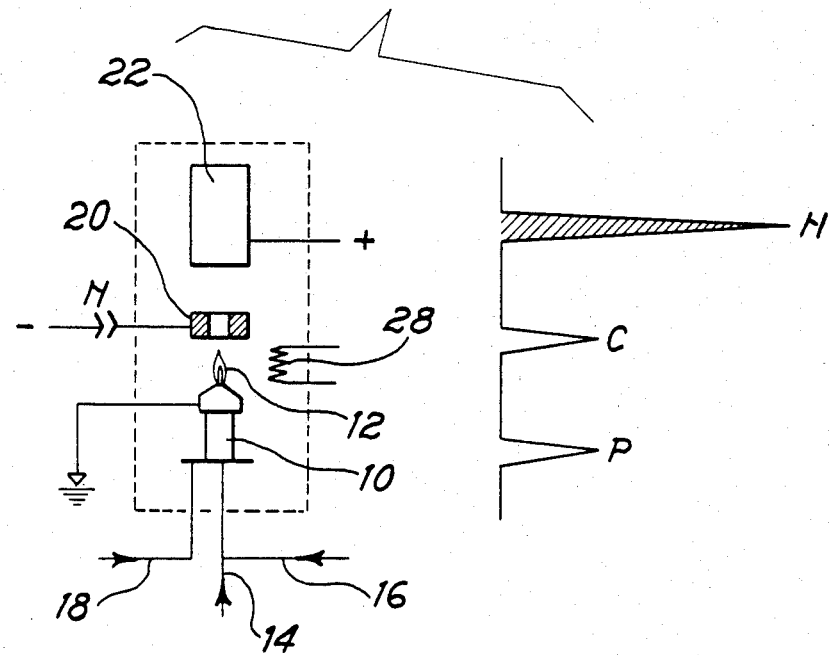
FIGS. 2, 3 and 4 are schematic diagrams showing the detector of FIG. 1 in its possible different operating conditions, with the indication of an example of typical chromatogram.
Figure 3:
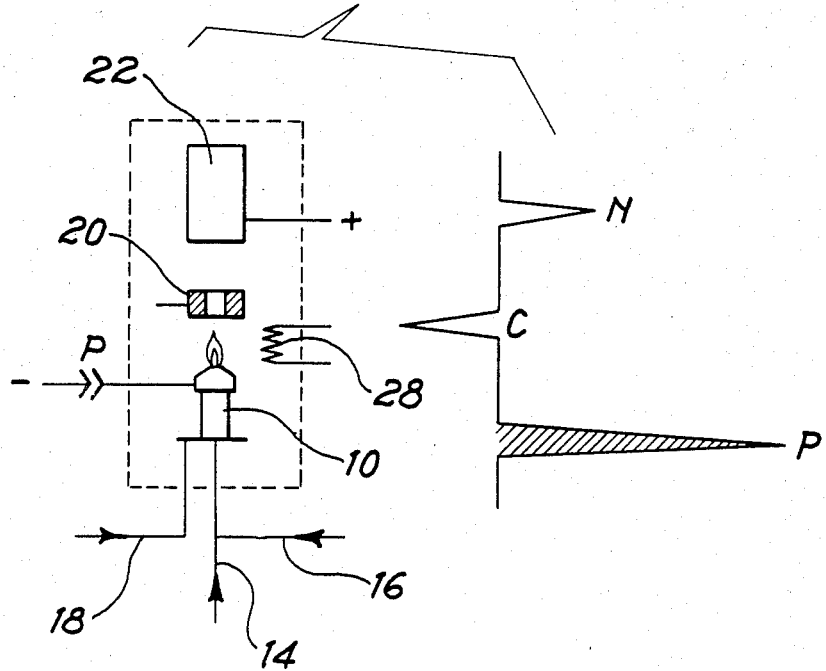
Figure 4:
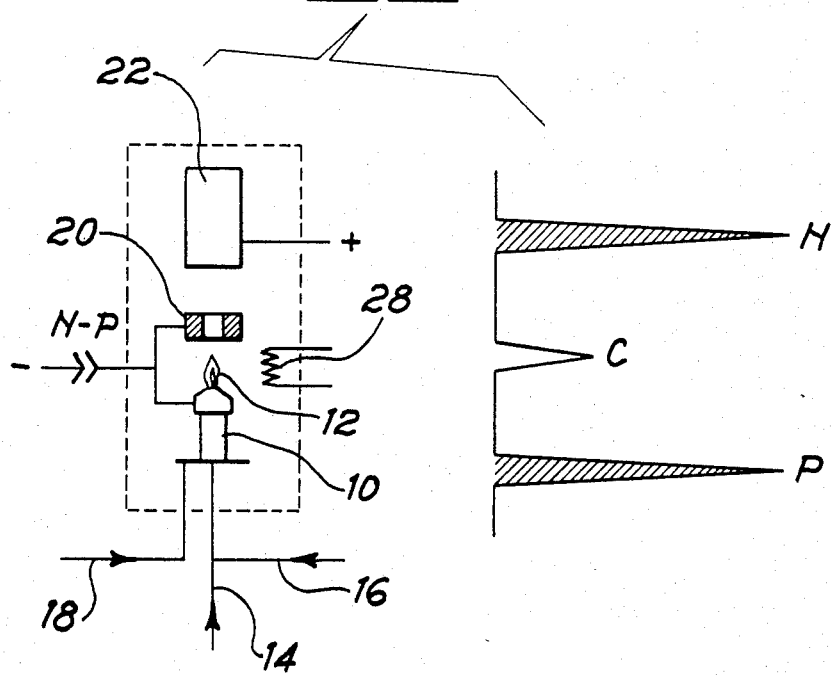

Different possible operating conditions of the detector according to the invention are schematically illustrated in FIGS. 2 to 4, in the first one of which it can be seen that the detector is in the condition previously indicated by N, in which the nitrogen compounds are detected (see the schematical chromatogram shown as an example besides the detector scheme). This is achieved in that the particular electrical connections allow to have minimum ground current. In FIG. 3, the ground current is at its maximum and the connection conditions are the ones previously indicated by P; in this situation, the responses to phosphorus compounds are detected, as indicated in the schematical chromatogram, where a negative response to carbon has been indicated. Finally, FIG. 4 illustrates the condition indicated by NP, which substantially corresponds to a standard operating condition, in which the sensitivity to compounds both of nitrogen and phosphorous with respect to carbon is detected.

As said hereinabove, the operating conditions to obtain the different sensitivities of the detector according to the invention require a constant supply of hydrogen flow and the use of helium as carrier gas of the sample.

Figures 5, 6:
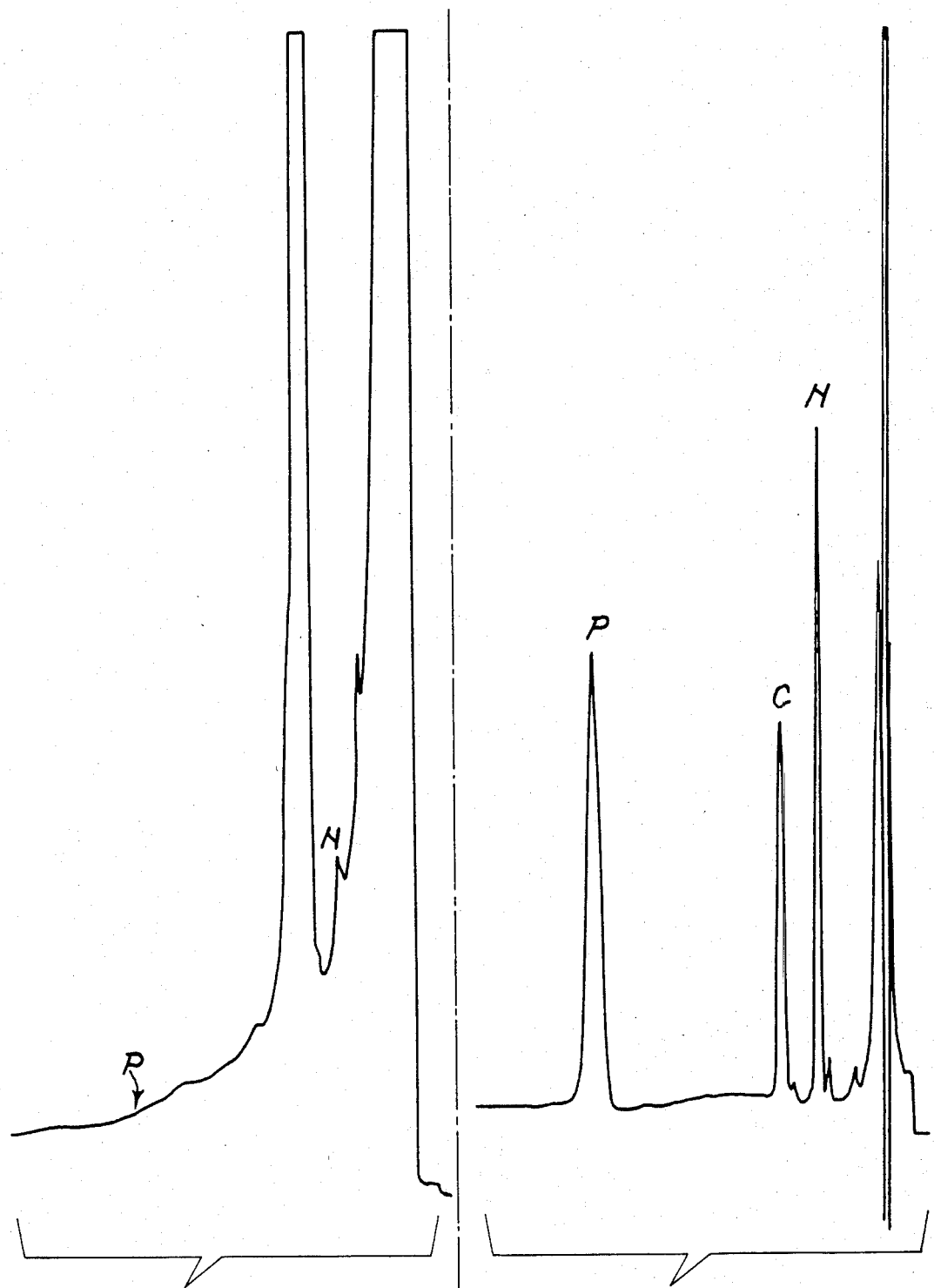
FIGS. 5 and 6 are two chromatograms obtained on the same sample with a conventional FID detector and with a detector according to the invention, respectively.

FIGS. 5 and 6 show two chromatograms obtained on the same sample, the first one with a conventional flame ionization detector (FID) and the second one with a detector according to the invention, set in the condition of sensitivity to N and P with respect to C. It can be clearly seen that in the first chromatogram (FIG. 5) only the peaks corresponding to C are detected and put into evidence, while in the second chromatogram, though obtained with an amplification equal to the half of the previous one, the latter peaks are attenuated and on the contrary the peaks P and N are enhanced. In particular, the reduction of the peak C and the increase of the peaks N (azobenzene) and above all P (malathion) have to be noticed.

The chromatograms of FIGS. 7 and 8 are, on the contrary, performed always on the same sample and with the same detector according to the invention, under conditions corresponding to N with positive C (FIG. 7) and to P with negative C, respectively (FIG. 8). From a comparison between the chromatograms, it can be immediately seen that the variations in the peaks allow identification of the compounds of the different chemical elements, as they have been indicated by N, P and C on the chromatograms, a posteriori, after the examination of the chromatograms themselves. Obviously, in case two subsequent chromatograms are not sufficient, it is possible to perform further analysis on the same sample, with a different adjustment of the thermionic detector. It must be noticed that the above mentioned peculiarities and features of the detector according to the invention can be modified in the details to adapt the same to different analytical situations, depending on the instruments and/or samples, without departing from the spirit and scope of the present invention.

We claim:

1. A modified flame thermionic detector for gas chromatographs, comprising:
   flame nozzle means for generating a flame along an axis from an eluant gas from a chromatography system and a combustible gas;
   collecting electrode means positioned coaxially to said flame nozzle means and connected to recording means for recording emitted current therefrom;
   excitation electrode means having an alkali source of thermions for being positioned along the flame axis between the flame and said collecting electrode means with said flame nozzle means and said excitation electrode means connected in a continuous current electrical circuit;
   said electrical circuit having a negative potential portion, a positive potential portion and a ground connection, and position switch means selectively switchable between a first position for connecting said flame nozzle means and said excitation electrode means to the negative potential of the circuit, a second position for connecting said flame nozzle means at the negative potential of the circuit and for electrically insulating said excitation electrode means with respect to the circuit, and a third position for connecting said excitation electrode means to the negative potential of the circuit and said flame nozzle means to ground; and
   mobile support means having said excitation electrode means mounted thereon for supporting said excitation electrode means in a movable manner for selectively positioning said excitation electrode means at will along the flame axis between said flame nozzle means and said collecting electrode means.

2. A thermionic detector according to claim 1, further comprising control means for maintaining the combustible gas flow supplied to the flame nozzle means constant, and for varying the selected operating positions of the switch means and of the excitation electrode means mobile support means.

3. A thermionic detector according to claim 1 consisting essentially of only a single flame nozzle means.

4. A thermionic detector according to claim 1, wherein said mobile support means for said excitation electrode means is mobile in a continuously adjustable manner.

5. A thermionic detector according to claim 4, further comprising control means for maintaining the combustible gas flow supplied to the flame nozzle means constant and for varying the selected operating positions of the switch means and of the excitation electrode means mobile support means.

6. A thermionic detector according to claim 1 or 4 further comprising gas supply means for supplying the gas eluting from the chromatograph to the flame nozzle means, wherein said gas supply means comprises a sample carrier gas supply of helium.

7. A thermionic detector according to claim 6, further comprising control means for maintaining the combustible gas flow supplied to the flame nozzle means constant and for varying the selected operating positions of the switch means and of the excitation electrode means mobile support means.

8. A modified flame thermionic detector for gas chromatographs, comprising:
   flame nozzle means for generating a flame along an axis from an eluant gas from a chromatography system and a combustible gas;
   collecting electrode means positioned coaxially to said flame nozzle means and connected to recording means for recording emitted current therefrom;
   excitation electrode means having an alkali source of thermions for being positioned along the flame axis between the flame and said collecting electrode means with said flame nozzle means and said excitation electrode means connected in a continuous current electrical circuit;
   said electrical circuit having a negative potential position, a positive potential position and a ground connection, and position switch means selectively switchable between a first position for connecting said flame nozzle means and said excitation electrode means to the negative potential of the circuit for detecting nitrogen-containing compounds and phosphorous containing compounds, a second position for connecting said flame nozzle means at the negative potential of the circuit and for electrically insulating said excitation electrode means with respect to the circuit for detecting phosphorous containing compounds, and a third position for connecting said excitation electrode means to the negative potential of the circuit and said flame nozzle means to ground for detecting nitrogen-containing compounds; and mobile support means having said excitation electrode means mounted thereon for supporting said excitation electrode means in a movable manner for selectively positioning said excitation electrode means at will along the flame axis between said flame nozzle means and said collecting electrode means.

* * * * *